United States Patent
McKenna et al.

(10) Patent No.: US 8,431,714 B2
(45) Date of Patent: Apr. 30, 2013

(54) SYNTHESIS OF DRUG CONJUGATES VIA REACTION WITH EPOXIDE-CONTAINING LINKERS

(75) Inventors: Charles E. McKenna, Los Angeles, CA (US); Boris A. Kashemirov, Los Angeles, CA (US); Joy Lynn F. Bala, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 1203 days.

(21) Appl. No.: 12/104,381

(22) Filed: Apr. 16, 2008

(65) Prior Publication Data

US 2008/0312440 A1 Dec. 18, 2008

Related U.S. Application Data

(60) Provisional application No. 60/912,051, filed on Apr. 16, 2007.

(51) Int. Cl.
C07F 9/28 (2006.01)
C07F 9/38 (2006.01)

(52) U.S. Cl.
USPC ............................................ 548/112; 546/22

(58) Field of Classification Search .................. 548/112; 546/22
See application file for complete search history.

(56) References Cited

PUBLICATIONS

Cede M. Bagi, "Targeting of therapeutic agents to bone to treat metastatic cancer", *Advanced Drug Delivery Reviews* (2005), vol. 57, No. 7, pp. 995-1010.

Gong Chen, et al., Reactivity of Functional Groups on the Protein Surface: Development of Epoxide Probes for Protein Labeling, *J.M. Chem. Soc.* (2003), vol. 125, pp. 8130-8133.

Feng Cheng, et al., "Inhibition of Isoprene Biosynthesis Pathway Enzymes by Phosphonates, Bisphosphonates, and Diphosphates", *J. Med. Chem. Society*, (2004), vol. 47, pp. 5149-5158.

M. D. Mignogna, et al., Case 2. *Osteonecrosis of the jaws associated with bisphosphonate therapy*, Section of Oral Medicine, Dept. of Odontostomatological and Maxillofacial Sciences, University Federico II, Naples, Italy: United States, (2006); pp. 1475-1477.

Keith Thompson, et al., "*Cytosolic Entry of Bisphosphonate Drugs Requires Acidification of Vesicles after Fluid-Phase Endocytosis*", Molecular Pharmacology (2006): vol. 69, No. 5, pp. 1624-1632.

Alison T. Ung, et al., "Synthesis of Fluorescent and Biotinylated Analogues of (1R,2S,3R)-2-Acetyl-4(5)-(1,2,3,4-Tetrahydroxybutyl)Imidazole", *Tetrahedron Letters* (1996), vol. 27 No. 34, pp. 6209-6212.

*Primary Examiner* — Charanjit Aulakh

(74) *Attorney, Agent, or Firm* — DLA Piper LLP (US)

(57) ABSTRACT

The present invention relates to drug derivatives and linkers. The invention specifically relates to compounds and methods of phosphonates and linkers, that are useful as carriers for imaging agents and useful in the treatment of various bone diseases.

19 Claims, No Drawings

SYNTHESIS OF DRUG CONJUGATES VIA REACTION WITH EPOXIDE-CONTAINING LINKERS

FIELD OF THE INVENTION

The present invention relates to compounds and methods of phosphonates and linkers.

BACKGROUND OF THE INVENTION

Imaging agents incorporating a targeting drug and visualizing moiety are indispensable in medical diagnostics and are invaluable aids in pharmacological drug development (9, 10, 23). Fluorophores absorbing in the visible region and emitting in the visible and near-infrared (IR) have found increasing application in this area owing to their scanning accessibility, convenience of use and sensitivity to detection (29). 5- or 6-Carboxyfluorescein (5-FAM, 6-FAM) and other fluorescent visible and near-IR labels are typically conjugated to a drug or protein by direct reaction of a primary amine of the drug or protein with a labels activated group (e.g. succinimidyl esters (SE), isothiocyanates (ITC), sulfosuccinimidyl esters (SSE), tetrafluorophenyl esters (TFP), sulfodichlorophenol esters (SC), etc.), thus forming an amide bond between the label and drug/protein (14). However, in cases when the parent drug structure lacks a primary amine group, often a linker (3) between the drug and label or structural modification to the drug (27) is necessary for labeling. In general, amido links are preferable to esters which may be labile to hydrolysis in vitro or in vivo.

Bone-targeting nitrogen-containing bisphosphonate drugs (N-BPs) such as (1-hydroxy-2-pyridin-3-ylethane-1,1-diyl)bis(phosphonic acid) 1, [hydroxy(1H-imidazol-1-yl)methylene]bis(phosphonic acid), {1-hydroxy-3-[methyl(pentyl)amino]propane-1,1-diyl}bis(phosphonic acid), (3-amino-1-hydroxypropane-1,1-diyl)bis(phosphonic acid), and (4-amino-1-hydroxybutane-1,1-diyl)bis(phosphonic acid) are extensively used in the clinic to treat osteoporosis and other disorders of bone metabolism (20, 21). Some bisphosphonate drugs have been shown to inhibit metastasis in bone cancer, and also to exhibit an anti-neoplastic effect on bone tumors (2, 7, 19). Alkylidenebisphosphonate drugs α-substituted with an aminoalkyl or N-containing heterocyclic group have been shown to inhibit specifically one or more enzymes of the mevalonic pathway; in at least some cases, the nitrogen atom is sufficiently basic to be protonated at physiological pH. X-ray crystallographic and modeling studies suggest that interaction of this nitrogen with target enzyme active site moieties contributes significantly to inhibitory potency and thus to the efficacy of this class of anti-osteoporotic drugs (5, 8, 11, 12, 15, 18). In contrast, the bone affinity is almost solely determined by the bisphosphonate moiety itself (18, 21, 28). Bisphosphonates have the general structure:

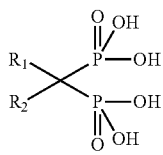

Fluorescently labeled bisphosphonate drugs can be useful in improving understanding of drug bone distribution, cellular distribution, and cell absorption selectivity. The clinically significant but thus far poorly understood anti-metastatic and anti-tumor cell effects of some bisphosphonates offers a further rationale for developing such imaging probes. Recent reports of a small number of previously unidentified osteonecrotic onsets that may be linked to prolonged therapy with at least one bisphosphonate also suggest an urgent requirement for improved understanding of bisphosphonate drug distribution in bone tissues (17, 22).

A conjugate of (4-amino-1-hydroxybutane-1,1-diyl)bis(phosphonic acid) with a near-IR fluorophore (Alexa Fluor® 488, commercially available from Molecular Probes, Inc.), attached to the drug by formation of a carboxamide link with the drug's ε-amino group, was recently described drug (25). In this process, formation of the amide link greatly reduces the basicity of the N atom, abolishing its ability to acquire a positive charge by protonation. A comparable acylation approach for conjugating heterocyclic N-BPs such as 1 (via its pyridine nitrogen) is not facile, and no fluorescently N-labeled versions of such compounds have been available to date, to the inventors' knowledge. The structure of 1-hydroxy-2-pyridin-3-ylethane-1,1-diyl)bis(phosphonic acid 1 is:

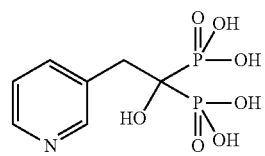 [SMILES: O=P(O)(O)C(O)(Cc1cccnc1)P(=O)(O)O]

SUMMARY OF THE INVENTION

In one embodiment, the invention relates to phosphonate drug or compound conjugates that may be used to study bone diseases.

In another embodiment, the invention relates to phosphonate drug or compound conjugates that may be used to study distribution of such drugs in bone tissues and cells.

In another embodiment, the invention relates to phosphonate drug or compound conjugates that may be used to treat bone diseases.

In a related embodiment, the invention relates to phosphonate drug or compound conjugates that may be used to detect bone diseases.

In accordance with one embodiment, the invention relates to methods of synthesizing phosphonate drug or compound conjugates that may be used to study bone diseases.

In accordance with another embodiment, the invention relates to methods of synthesizing phosphonate drug or compound conjugates that may be used to study distribution of such drugs in bone tissues and cells.

In accordance with another embodiment, the invention relates to methods of synthesizing phosphonate drug or compound conjugates that may be used to treat bone diseases.

In accordance with a related embodiment, the invention relates to methods of synthesizing phosphonate drug or compound conjugates that may be used to detect bone diseases.

In a closely related embodiment, the invention relates to methods of using phosphonate drug conjugates to study bone diseases.

In another closely related embodiment, the invention relates to methods of using phosphonate drug or compound conjugates to study distribution of such drugs in bone tissues and cells.

In another closely related embodiment, the invention relates to methods of using phosphonate drug or compound conjugates to treat bone diseases.

In yet another closely related embodiment, the invention relates to methods of using phosphonate drug or compound conjugates to detect bone diseases.

DETAILED DESCRIPTION OF THE INVENTION

As used herein the term "bone disease" refers to or describes any affliction that involves the skeletal system and encompasses any condition that is associated with an impairment of the normal state of the skeletal system including congenital defects, pathological conditions such as cancer, and responses to environmental factors and infectious agents (bacterial, viral, etc.). Examples of bone diseases include but are not limited to osteoporosis, Paget's disease, metastatic bone cancers, hyperparathyroidism, rheumatoid arthritis, algodystrophy, stemo-costoclavicular hyperostosis, Gaucher's disease, Engleman's disease, disorders of bone metabolism, and the like.

The term "phosphonate" describes organic compounds containing one or more C—PO(OH)$_2$ or C—PO(OR)$_2$ (with R=alkyl, aryl) groups. The "phosphonate" as used herein preferably refers to analogs of phosphonate. Examples of phosphonates include but are not limited to bisphosphonates, phosphonoacetates, methylenebisphosphonates, phosphonocarboxylates, nitrogen-containing bisphosphonates, and the like.

Phosphonates are preferably fluorescently labeled or conjugated with fluorophores, visible or near-infrared imaging agents. Examples of fluorophores or near-infrared imaging agents include but are not limited to Alexa Fluor dyes, Cye dyes, IRDyes, other fluorophores, near-infrared imaging agents, and the like. More specifically, fluorophores refer to 5-carboxyfluorescein (5-FAM), 6-carboxyfluorescein (6-FAM), AMCA-X, Rhodamine Red-X, and the like, and near-infrared agents refer to Alexa Fluor 647, and the like.

Fluorescently labeled phosphonates may be used to improve the understanding of drug bone distribution, cellular distribution, and cell absorption selectivity.

The term "linker" refers to the moiety between the phosphonate and another compound or structural modification to the phosphonate that allows for conjugation of the phosphonate. Phosphonates may be linked to compounds, imaging agents, structures, or other moieties that may be used in drug delivery. Examples include but not limited to drugs, beads, fluorescent labels, and the like.

Furthermore, phosphonate conjugates or compounds may used in a variety of ways. For example, conjugates or compounds may be used as a drug for the treatment of bone diseases or as a diagnostic for the detection of bone disease. Conjugates or compounds can also be used to study bone disease and the distribution of phosphonates in bone tissues, and bone cells.

Fluorescently labeled or conjugated phosphonates or compounds of the invention are formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

In one embodiment, the compounds are prepared with carriers that will protect the compounds against rapid elimination from the body, such as a controlled release formulation, including implants and microencapsulated delivery systems. Therapeutic agents, may also comprise siRNAs conjugated to cationic polypeptides, amphipathic compounds, polycations, liposomes or PEGylated liposomes. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

It is advantageous to formulate oral or parenteral compositions in dosage unit form for ease of administration and uniformity of dosage. "Dosage unit form," as used herein, refers to physically discrete units suited as unitary dosages for the subject to be treated, each unit containing a predetermined quantity of an active compound calculated to produce the desired therapeutic effect in association with the required pharmaceutical carrier.

The dosage required for treating a subject depends on the choice of the route of administration, the nature of the formulation, the nature of the subject's illness, the subject's size, weight, surface area, age, and sex, other drugs being administered, and the judgment of the attending physician. Wide variations in the needed dosage are to be expected in view of the variety of compounds available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

To practice methods of treatment, fluorescently labeled phosphonate compounds are administered to a human or other mammal in need thereof a therapeutically effective amount of the compound. Indications appropriate to such treatment include bone diseases that include but are not limited to osteoporosis, Paget's disease, metastatic bone cancers, hyperparathyroidism, rheumatoid arthritis, algodystrophy, stemo-costoclavicular hyperostosis, Gaucher's disease, Engleman's disease, disorders of bone metabolism, and the like.

To practice methods relating to the study of bone disease or distribution of phosphonates in bone tissue or cells, fluorescently labeled compounds can be used in various model systems, including enzymatic and cellular assays as well as in vivo. For enzymatic studies, fluorescent compounds can be pre-incubated with enzyme, and the reaction products can be detected according to standard procedures. For imaging of compounds of distribution in cells, fluorescent compounds can be added to cell culture medium using standard methods known to those skilled in the art, and then visualized by methods such as confocal microscopy. For in vivo studies, compounds incorporating a near-IR imaging agent may be administered intravenously or by other appropriate means to the animal and subsequently visualized with NIR fluorescence imaging systems. Alternatively, compounds containing fluorescent labels may be administered and the distribution of the compound in bone tissues or organs determined postmortem.

To practice the methods relating to methods of synthesizing fluorescently labeled analogs of phosphonates, the synthesis of 1-(3-amino-2-hydroxypropyl)-3-(2-hydroxy-2,2-diphosphonoethyl)pyridinium trifluoroacetate 6 may be used as an example. The linking strategy is centered on the reaction of N-t-BOC protected 1,2-epoxy-3-aminopropane 4 to the nitrogen of the pyridine ring of 1 (Scheme 1). The low solubility of 1 in organic solvents limits any reaction involving this compound to aqueous environments; however, "linker" 4 is highly soluble in nonpolar solvents. Surprisingly, the N-alkylation reaction occurs with high regioselectivity and mild reaction conditions (aqueous conditions, pH 5-6, 35-45° C.), unlike the previously reported O-alkylation of a bisphosphonic acid with diethyloxiranylmethylamine (aqueous conditions, near neutral pH, 60-70° C.) (6). Surprisingly, at this temperature, the inventors' reaction yields only 10% O-alkylation and 90% N-alkylation and at 40° C., the reaction proceeds to nearly quantitative yield to afford the N-alkylated product 5 with less than 1% O-alkylation.

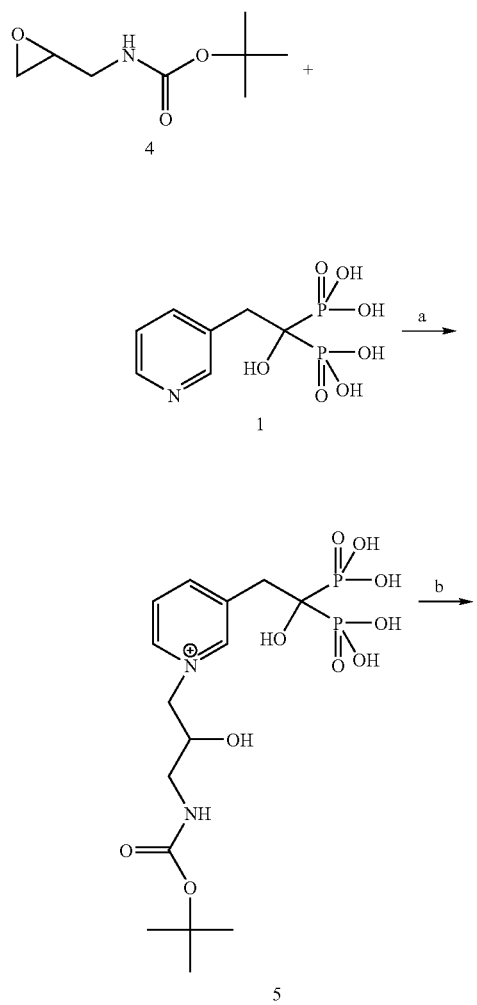

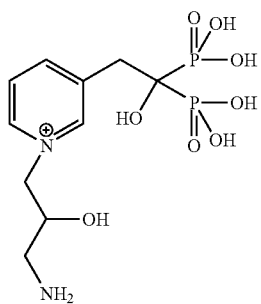

(a) $H_2O/MeOH$, 40° C.; (b) 1:1 TFA: $H_2O$, 4 hrs, rt.

Intermediate 5 then undergoes subsequent deprotection with TFA to afford novel compound 6 as a trifluoroacetate salt. This invention not only introduces a primary amine to the parent drug for facile conjugation to activated groups of fluorescent labels or other conjugate partners, but also generates a permanent positive charge on the pyridinium nitrogen and introduces an additional hydroxyl group, which may increase the drug's hydrophilicity. Additionally, by avoiding conjugation of the linker group via the phosphoryl oxygens, the new compounds can retain bone affinity.

Analog 6 is then easily coupled to a group susceptible to reaction with a primary amine, for example the succinimidyl ester of 5(6)-carboxyfluorescein (5(6)-FAM, SE, 7) under appropriate conditions (Scheme 2).

Several purification methods may be utilized to isolate the product, including size exclusion chromatography, reverse-phase HPLC, and TLC on silica gel.

For example, Sephadex G10 columns eluted with TEAAc buffer can be used to remove low molecular weight impurities, and the first eluting orange band of the product collected. To ensure complete separation from both free label and unlabeled drug, a second purification step may be used, such as reverse-phase HPLC which was used to obtain pure compound 8. Although this purification sequence granted the purified product, poor separation between the undesired compounds and the inventors' product during size-exclusion chromatography lowered product yield.

Therefore, to remove free label, the inventors also developed a facile purification method by TLC with 100% MeOH as the eluant. Extraction of the product from silica is performed with water as the solvent. Although this method may not fully extract all of the desired compound from silica, it is rapid and convenient. NMR spectra of the extracts only showed broad peaks, but treatment with Chelex to remove any traces of metal co-extracted from the silica, resulted in NMR spectra of good quality that well characterized the structure and purity of the product.

To remove unlabeled 6, reverse-phase HPLC may be used advantageously, the unlabeled drugs having much shorter retention times than the product. Additionally, the 5- and 6-isomers (9 and 10, respectively) of the labeled product can be separated by HPLC, a method more cost effective than directly synthesizing these products from their respective isomerically pure fluoresceins purchased commercially.

Scheme 2.

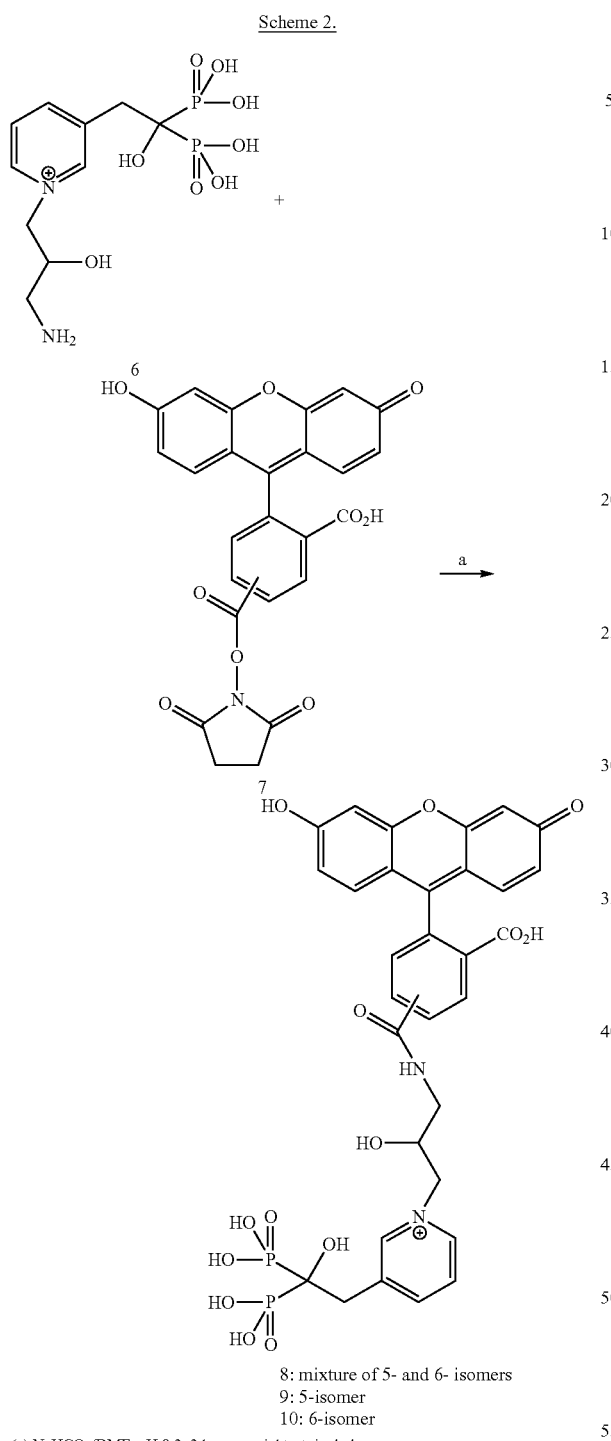

8: mixture of 5- and 6- isomers
9: 5-isomer
10: 6-isomer (a) NaHCO₃/DMF, pH 8.3, 3 hrs-overnight, rt, in darkness.

Triethylammonium acetate is an appropriate buffer for such HPLC separations. However, the higher volatility of triethylamine versus acetic acid causes a drop in pH, resulting in pH 4-5, when removing the buffer under vacuum. The inventors found that, especially for larger scale purifications, the desired compounds tend to precipitate under these conditions since they are much more water-soluble in neutral to basic pH. Although the acetate buffer appears to be satisfactory in preparation of smaller amounts of compound, the inventors have identified triethylammonium carbonate as a more suitable buffer for maintaining a basic pH and thus avoiding unwanted precipitation of the desired product.

This same synthetic strategy was applied to two analogs of 1: 2-hydroxy-2-phosphono-3-pyridin-3-ylpropanoic acid 11, a phosphonocarboxylate analog of 1 where one phosphonate moiety is replaced with a carboxyl group, and (2-pyridin-3-ylethane-1,1-diyl)bis(phosphonic acid) 12, where the α-hydroxy is replaced with H (Scheme 3). Isomers of 11 and 12 may also be separated by HPLC although in this case, we chose to synthesize pure isomers of 11 from isomerically pure starting materials. All FAM-labeled compounds have been characterized by high resolution mass spectrometry and $^1$H and $^{31}$P NMR, UV absorption, and fluorescence emission spectra. The structures for 11 and 12 are:

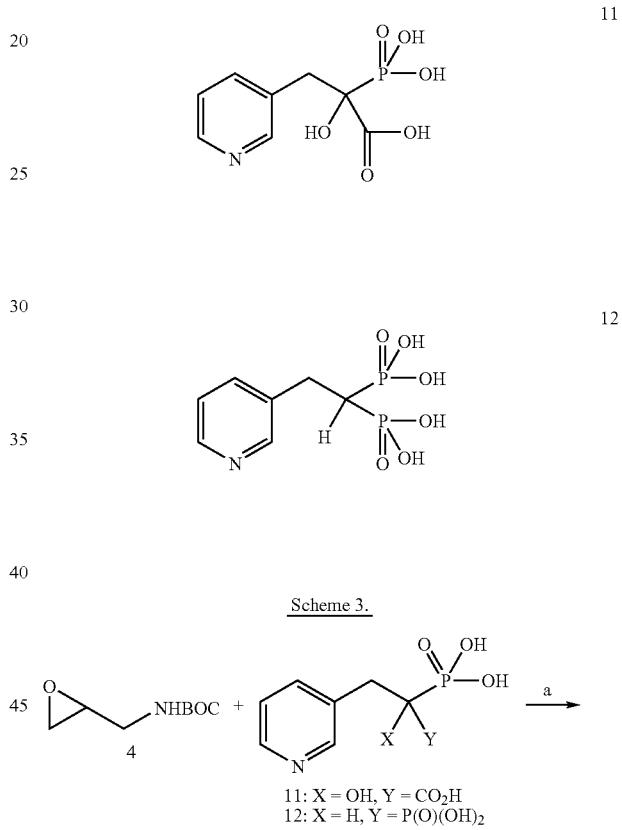

Scheme 3.

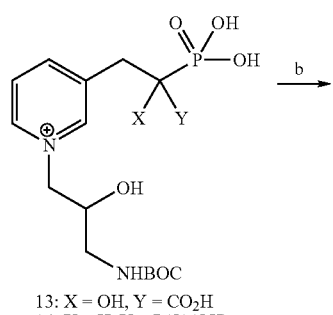

11: X = OH, Y = CO₂H
12: X = H, Y = P(O)(OH)₂

13: X = OH, Y = CO₂H
14: X = H, Y = P(O)(OH)₂

-continued

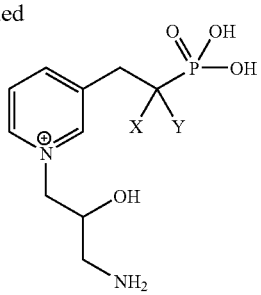

15: X = OH, Y = CO₂H
16: X = H, Y = P(O)(OH)₂

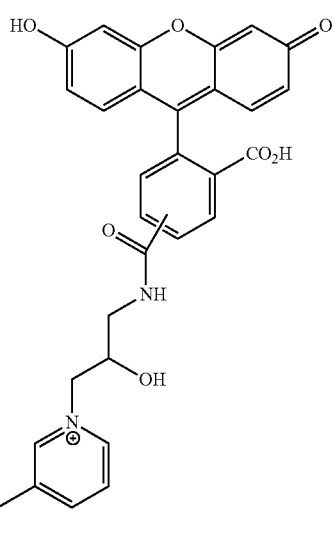

17: X = OH, Y = CO₂H, a mixture of 5- and 6- isomers
18: X = OH, Y = CO₂H, 5- isomer
19: X = OH, Y = CO₂H, 6- isomer
20: X = H, Y = P(O)(OH)₂, a mixture of 5- and 6- isomers (a) H₂O/MeOH, 40° C.; (b) 1:1 TFA: H₂O, 4 hrs, rt; (c) 7, NaHCO₃/DMF, pH 8.3, 3 hrs-overnight, rt, in darkness.

UV spectra (taken on a DU 800 spectrophotometer) of all FAM-labeled compounds (8-10 and 17-20) exhibit similar spectra to 5(6)-FAM, which has a reported $\epsilon_{492}$=73,000 $M^{-1}cm^{-1}$ at pH 7.2 (13,16). However, there is about a 35% larger $\epsilon$ at 260 nm due to a contribution from the pyridinium chromophore ($\epsilon$=14,427 $M^{-1}cm^{-1}$ at 262 nm) (24).

Fluorescence emission spectra (taken on a Jobin Yvon Horiba FluoroMax-3 fluorometer, with excitation wavelength at 490 nm and maximum emission at ~520 nm) of the FAM-labeled compounds typically show a loss of 10-20% of fluorescence intensity. Although care was given to ensure minimal light exposure while working with all labeled products, the slight decrease in fluorescence may be due to some bleaching during work-up, or may be an inherent characteristic of the FAM-labeled compounds. For imaging purposes, the decrease does not affect the utility of the compounds.

To study the stability of 8, the compound and 5- and 6-FAM, all in 0.1 N phosphate buffer (pH 7.2), were stored in a freezer and in darkness for one week. Both solutions were analyzed by TLC on silica gel with 100% methanol as the eluant. The inventors' compound showed only one spot at the baseline (UV detection at 365 nm), which corresponds to desired product 8. The presence of 5(6)-FAM (which does not remain on the baseline under these TLC conditions but rather travels quickly with the solvent) was not detected in the solution containing compound 8, thus indicating that 8 is stable and does not hydrolyze to release free label. In addition, the same solutions were kept for an additional 6 days at room temperature and no change was seen by analytical TLC. Small aliquots of the phosphate solutions were also diluted in two other buffers: 50 mM HEPES (pH 7.0) and 50 mM TRIS (pH 7.7). The resulting new buffer solutions were then kept at room temperature overnight and analyzed by TLC. No decomposition of the inventors' compound was observed.

Chen et al. previously synthesized a fluorescent probe for proteins, derived from R-glycidol and 5-FAM, SE and 5(6)-FAM, SE (4). Then, the fluorescently labeled epoxide (in slight excess) reportedly reacts with a specific histidine residue of their target protein in high yields (4). In contrast, the inventors' approach involves the opening of the epoxide by the heterocylic nitrogen first, followed by subsequent conjugation to the fluorescent label. This method may be more cost efficient than synthesizing labeled epoxides, especially in cases involving more expensive commercially available imaging agents. Moreover, the previously reported method utilizes an ester bond to connect the epoxide moiety to the rest of the probe, which is more labile to hydrolysis under physiological conditions than an amide bond formed in the present synthesis. Finally, this method did not involve phosphonates attached to a heterocyclic nitrogen group.

Compounds 1, 11, and 12 may be labeled with the mixture of fluorescein isomers and also using isomerically pure 7. Compounds 8-10 fluoresce with a green color that appears very similar to the green fluorescence emitted by 7. In order to study compounds 1, 11, and 12 within the same biological assay, each compound can advantageously be labeled with differently colored fluorescent emitters. For example, 11 and 12 can be labeled with the following fluorescent labels: Rhodamine Red-X (RhR-X) and 6-((7-amino-4-methylcoumarin-3-acetyl)amino)hexanoic acid (AMCA-X). The fluorescent color of RhR-X is red-orange while AMCA-X is blue. By labeling each drug with a different colored label, such as labeling 11 with AMCA-X and 12 with RhR-X, the new imaging probes may be simultaneously visualized with FAM-labeled 8 within the same biological assay. Alternatively, the effect of the label on the properties of the drug can be ascertained by preparing differently labeled versions of the same drug. Many other useful applications of the invention may be made. For example, drugs that may not be susceptible to this labeling method, such as phosphonate compounds lacking a linkable nitrogen, may be indirectly imaged by their ability to displace a labeled phosphonate compound from a site of binding such as bone. Compounds 23, 24, and 25 can be synthesized and purified by methods similar to those described for FAM-labeled compounds (Scheme 4-5).

The Linking Strategy

To form the stable amido linkage to the FAM label, a terminal oxiranyl amine is required. For this purpose, the corresponding allylamine 2 may be first converted to the N-t-BOC protected compound 3. Epoxidation with m-chloroperbenzoic acid provides the oxirane 4. 1 was dissolved in water and the pH adjusted to 6.4 with 1 N NaOH. This solution was combined with 4 in MeOH, yielding 5, which was then deprotected with TFA, giving 6. To commercially available 5(6)-FAM, SE (Sigma Aldrich) in fresh and anhydrous DMF was added 6 in $NaHCO_3$ (pH 8.3-8.5) and the reaction mixture stirred at room temperature for 3 hours. The reaction mixture can also be analyzed conveniently by silica gel TLC with UV illumination (100% MeOH), the fluorescent labeled product being easily distinguishable (Rf 0.0) from 5(6)-FAM (Rf 1.0), a side product from the hydrolysis of the activated ester form. After removal of DMF and water under vacuum and redisolution in 50 mM TEAAc (pH 9), the crude reaction mixture was eluted through a G-10 Sephadex column (3 cm×40 cm) with 50 mM TEAAc (pH 9) to remove traces FAM isomers. Each fraction eluted is analyzed by silica gel TLC according to the method described above. All fractions not containing 5(6)-FAM by this analysis method are then additionally purified and separated into its individual isomer components by preparative reverse-phase HPLC with the following conditions: Dynamax C-18 column, flow rate 8.0 mL/min of 10% MeOH in 0.1 N TEAAc (pH 7) to 40% of 75% MeOH in 0.1 N TEAAc (pH 7) in 12 min, increasing to 70% of 75% MeOH in 0.1 N TEAAc in 100 min, UV detection at 260 nm. 9 (elution at 27 min) and 10 (elution at 44 min) are collected separately, dried, and isolated as a stable, reddish-orange solids, readily soluble in water and stable under neutral conditions and at room temperature for at least 24 hours.

A wide range of imaging agents, such as fluorescent and near-IR labels commercially available as activated esters, may be incorporated into our invented compounds. These activated esters will allow a person of ordinary skill in the art to easily conjugate our linker compounds to any desired label. For example, Alexa Fluor® 647, succinimidyl ester 26 (31), a near-IR label, was successfully conjugated to 6 yielding compound 27, purified by HPLC, and characterized by mass spectrometry and NMR, TV absorption, and fluorescence emission spectra (Scheme 6).

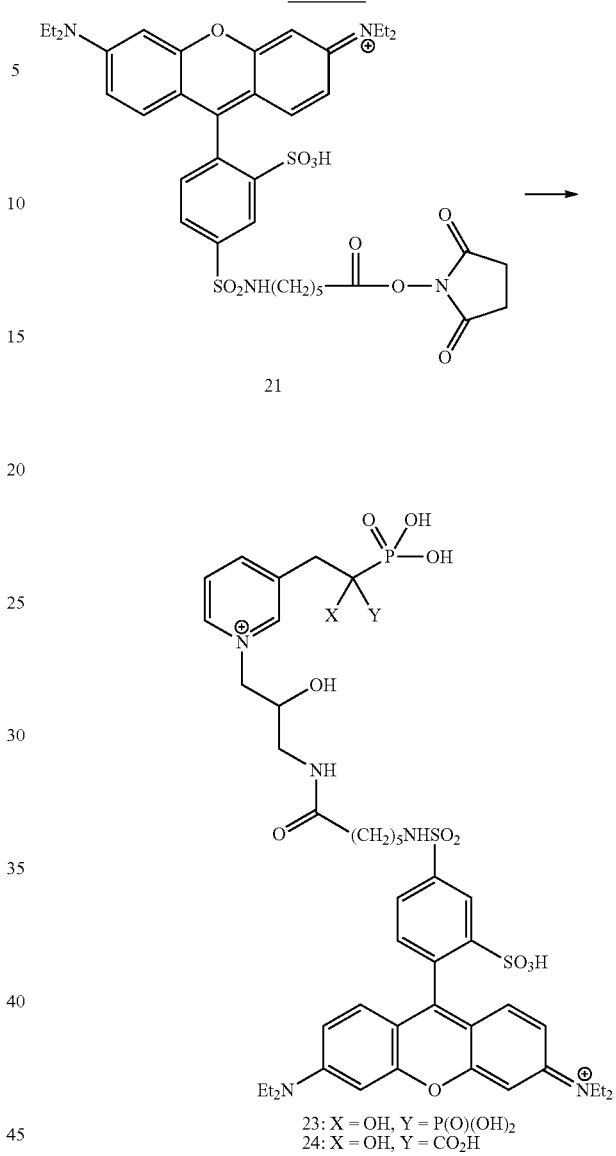

Scheme 4.

21

23: X = OH, Y = P(O)(OH)$_2$
24: X = OH, Y = CO$_2$H 6 or 15, NaHCO$_3$/DMF, pH 8.3, 3 hrs-overnight, rt, in darkness.

Scheme 5.

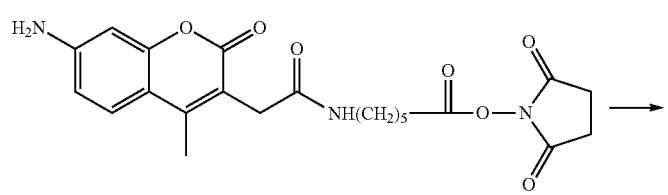

22

-continued
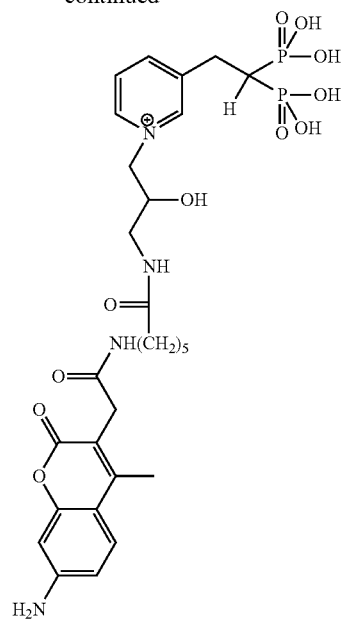
25
16, NaHCO₃/DMF, pH 8.3, 3 hrs-overnight, rt, in darkness.
Scheme 6.
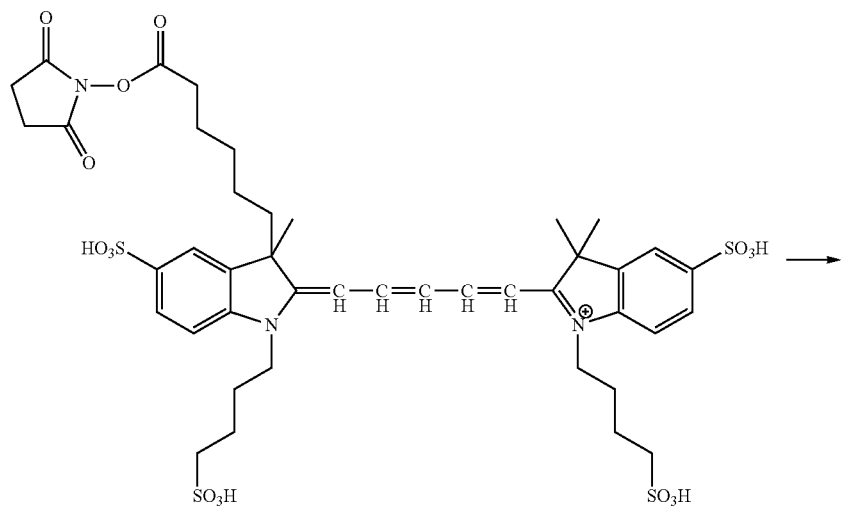
26

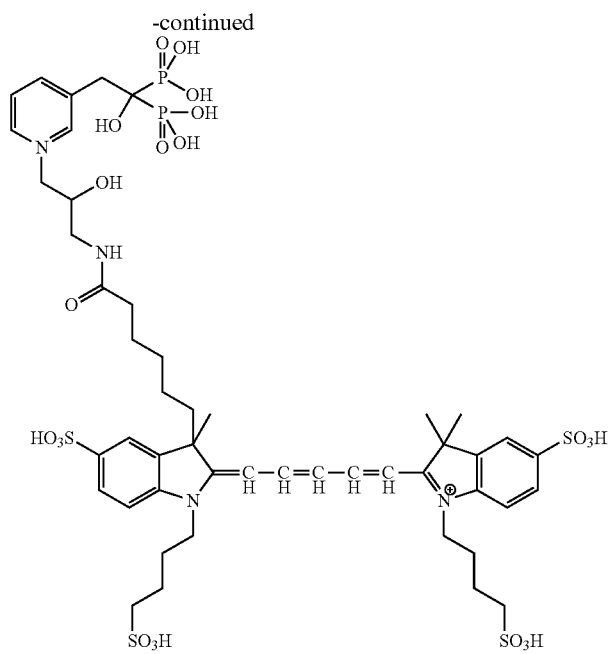

27

6, NaHCO$_3$/DMF, pH 8.3, 3 hrs-overnight, rt, in darkness.

The N-alkylation to form a pyridinium ring through this epoxide technology is a highly effective approach that gives excellent regioselectivity and yields, providing pure materials. This chemistry makes possible a general synthesis of previously unavailable fluorescently labeled N-BPs. Thus, it is applicable to other types of nitrogen besides pyridinyl nitrogens, such as the tertiary nitrogens in {1-hydroxy-3-[methyl(pentyl)amino]propane-1,1-diyl}bis(phosphonic acid) (28), and nucleophilic nitrogens in other heterocyclic compounds, such as that in [hydroxy(1H-imidazol-1-yl)methylene]bis(phosphonic acid) (29) or the in the bicyclic structure found in (1-hydroxy-2-imidazo[1,2-a]pyridin-3-ylethane-1,1-diyl)bis(phosphonic acid) (30). The structures of 28, 29, and 30 are:

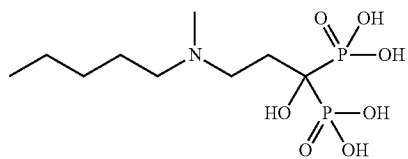

28

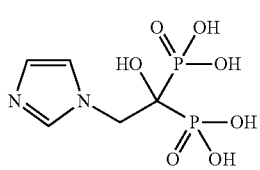

29

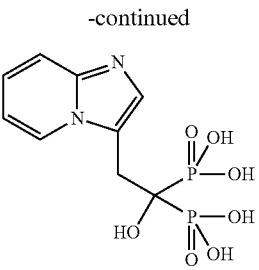

30

This approach is not restricted only to N-bisphosphonates, as already demonstrated by the synthesis of a fluorescent phosphonocarboxylate (PC) analog (17-19 and 24), but may also be applied for any type of compound containing the mildly nucleophilic heterocyclic nitrogens or tertiary nitrogens. In cases where such cyclic systems are absent but a phosphorus-oxygen (P—O) bond is still present in the parent drug, the conditions of this epoxide chemistry may be altered to favor O-alkylation, thus generating the linker through the P—O bond. Additionally, this technology may be applied to similar BP and PC compounds with no known pharmacological activity in cases where an active drug may not be needed. Thus, the invention may be applied to an extensive range of compounds (including BPs, PCs, other phosphorus-containing compounds, and compounds with tertiary nitrogens or nitrogen-containing heterocycles) to introduce a "linker" moiety necessary for direct acylation or other compatible conjugation reaction with any other groups, including imaging agents or other moieties such as drugs requiring or benefiting from delivery to bone.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Synthesis of tert-Butyl N-allylcarbamate (3)

Tert-butyl N-allylcarbamate was synthesized according to the method of Rocheblave (30). 2.3 mL (30 mmol, 1 equiv) of freshly distilled allylamine 2 in 10 mL $CH_2Cl_2$ was cooled in an ice bath (0° C.). To this cold solution was added 6.54 g $Boc_2O$ (30 mmol, 1 equiv) in 20 mL $CH_2Cl_2$. The solution was brought to room temperature and stirred for 4 hours.

The reaction mixture was then diluted with additional $CH_2Cl_2$ and washed with 5% citric acid solution followed by brine. The organic layer was dried over $Na_2SO_4$ and concentrated in vacuo, yielding 3.29 g (68% yield) of 3.

$^1H$ NMR (500 MHz, $CDCl_3$): δ1.38 (s, 9H), 3.68 (brs, 2H), 4.53 (brs, 1H), 5.02-5.16 (m, 2H), 5.72-5.84 (m, 1H).

Synthesis of tert-butyl N-(2-oxiranylmethyl)carbamate (4)

Tert-butyl N-(2-oxiranylmethyl)carbamate was synthesized according to the method of Rocheblave (30). 1 g (6 mmol, 1 equiv) of N-t-BOC protected 3 was dissolved in 50 mL dry $CH_2Cl_2$. The solution was brought to 0° C. and kept cold upon addition or 2.8 g (12 mmol, 2 equiv) MCPBA. The solution was then brought to room temperature and stirred overnight.

About half of the reaction mixture was taken and diluted with additional ~80 mL of $CH_2Cl_2$. The solution was washed with 10% $Na_2SO_3$, followed by washing with saturated $NaHCO_3$ 3 times, and finally by washing with water. The organic layer was dried over $Na_2SO_4$ and concentrated in vacuo, yielding crude epoxide 4. By $^1H$ NMR, approximately 85% yield was achieved.

$^1H$ NMR (400 MHz, $CDCl_3$): δ 1.44 (s, 9H), 2.59-2.78 (brm, 2H), 3.04-3.54 (m, 3H), 4.75 (brs, 1H).

General Synthesis of N-Alkylated Drug Analogs

The parent drug is dissolved in water and pH is adjusted to ~6 with 1 N NaOH. Epoxide 4 is dissolved in minimal MeOH, and the reaction mixture is heated at 35-50° C. for 18-45 hours. Upon addition of the methanol solution to the water solution, slight precipitation occurs. Solubility is increased with slight heating and as reaction progresses. The reaction is monitored by $^{31}P$ NMR and can also be monitored by analytical reverse-phase HPLC. After 90-95% of the desired product is obtained, the solvent is removed in vacuo, and the resulting white powder is washed with diethyl ether, filtered and dried. Standard deprotection is performed with TFA. After the reaction mixture is stirred for 3-4 hours at room temperature, the solvent is removed in vacuo, and the resulting crystals are washed with diethyl ether and methanol to yield the appropriate drug-linker analog, used without additional purification, for labeling reactions.

Synthesis of 1-(3-amino-2-hydroxypropyl)-3-(2-hydroxy-2,2-diphosphonoethyl)pyridinium trifluoroacetate (6)

287 mg of monosodium salt of 1 (0.9 mmol, 1 equiv) was dissolved in 4 mL water and pH adjusted to 6.2 with 1 N NaOH. 163 mg of 4 (0.9 mmol, 1 equiv) in minimal MeOH was added. Slight precipitation upon addition occurs, but will slowly disappear as reaction progresses. The reaction mixture was stirred at 40° C. for 18.5 hours, yielding 90% of 5 by $^{31}P$ NMR. The solvent was removed in vacuo, and the remaining solids were washed with ether, filtered, and dried in a dessicator. The remaining solids 5 were then used without further purification.

$^1H$ NMR (400 MHz, $D_2O$): δ 1.27 (s, 9H), 3.07-3.30 (m, 4H), 3.95-4.03 (m, 1H), 4.18-4.27 (dd, J=13.7 Hz, 3.7 Hz, 1H), 4.58-4.65 (part. obscured by HDO, about 1H), 7.75 (t, J=6.8 Hz, 1H), 8.39 (d, J=7.8 Hz, 1H), 8.43 (d, J=6.5 Hz, 1H), 8.65 (s, 1H). $^{31P}\{^1H\}$ NMR (400 MHz, $D_2O$): δ 16.33 (d, J=21.1 Hz, 1P), 16.55 (d, J=21.1 Hz, 1P).

The entire sample of 5 was dissolved in 3 mL water. 3 mL TFA was slowly added, and the solution was stirred at room temperature for 3 hours. According to NMR, 100% yield is achieved of 6. The solvent was then removed in vacuo, and the resulting solids were washed with ether, filtered, and dried, yielding 6 as white crystals. 6 was then used without further purification.

$^1H$ NMR (400 MHz, $D_2O$): δ 3.01 (t, J=11 Hz, 1H), 3.31 (d, J=12.6 Hz, 1H), 3.39 (t, J=11.6 Hz, 2H), 4.25-4.33 (m, 1H, 4.36-4.44 (br, 1H), 7.88 (t, J=6.6 Hz, 1H), 8.48 (d, J=8.0 Hz, 1H), 8.58 (d, J=5.5 Hz, 1H), 8.77 (s, 1H). $^{31}P\{^1H\}$ NMR (500 MHz, $D_2O$): δ 16.04 (d, J=27.5 Hz, 1P), 16.40 (d, J=27.5 Hz, 1P).

Synthesis of 1-(3-amino-2-hydroxypropyl)-3-(2-carboxy-2-hydroxy-2-phosphonoethyl)pyridinium trifluoroacetate (15)

0.52 g of 11 (2 mmol, 1 equiv) was dissolved in 10 mL water and pH adjusted to 5.9 with 1 N NaOH. 0.445 g of 4 (2.6 mmol, 1.3 equiv) in minimal MeOH was added. Slight precipitation upon addition occurs, but will slowly disappear as reaction progresses. The reaction mixture was stirred at 50° C. for 6 hours and then stirred at room temperature overnight, yielding 90% of 13 by $^{31}P$ NMR. The solvent was removed in vacuo, and the remaining solids were washed with ether, filtered, and dried in a dessicator. The remaining solids 13 were then used without further purification.

$^1H$ NMR (400 MHz, $D_2O$): 1.27 (s, 9H), 3.00-3.23 (m, 3H), 3.45 (dd, J=14.2 z, 3.6 Hz, 1H), 3.91-4.00 (m, 1H), 4.19-4.27 (m, 1H), 4.58-4.64 (br, 1H), 7.78 (dd, J=8.3 Hz, 6.2 Hz, 1H), 8.24-8.29 (m, 2H), 8.47 (d, J=6.0 Hz, 1H), 8.49-8.53 (brd, 1H). $^{31}P\{^1H\}$ NMR (400 MHz, $D_2O$): δ 14.96 (s, 1P), 14.98 (s, 1P).

The entire sample of 13 was dissolved in 50:50 water:TFA. The solution was stirred at room temperature for 4 hours. According to NMR, 100% yield is achieved of 15. The solvent was then removed in vacuo, and the resulting solids were washed with ether, filtered, and dried, yielding 15 as white crystals. 15 was then used without further purification.

$^1H$ NMR (400 MHz, $D_2O$): δ 2.90 (m, 1H), 3.18-3.28 (m, 2H), 3.50 (m, 1H), 4.14-4.22 (m, 1H), 4.31-4.40 (m, 1H), 4.71-4.74 (m, 1H), 7.87 (dd, J=8.3 Hz, 6.1 Hz, 1H), 8.34-8.39 (brd, 1H), 8.56-8.68 (m, 2H). $^{31}P\{^1H\}$ NMR (400 MHz, $D_2O$): δ 12.53 (s, 1P), 12.62 (s, 1P).

Synthesis of 1-(3-amino-2-hydroxypropyl)-3-(2,2-diphosphonoethyl)pyridinium trifluoroacetate (16)

38 mg 12 (1.4 mmol, 1 equiv) was dissolved in 1 mL water and pH brought to 5.4 with 1 N NaOH. To this solution was added 34 mg of 4 (1.8 mmol, 1.2 equiv) in minimal MeOH. The reaction mixture was stirred at 40° C. overnight, and the reaction was followed by $^{31}P$ NMR. After 19 hours, 20% of starting material 12 remained. Thus, an additional 7 mg of 4 in MeOH was added to the reaction mixture. After 42 hours, 90% of the desired product was obtained. The solvent was removed in vacuo, and the resulting white powder was washed with diethyl ether, filtered, and dried. The remaining solids 14 were used without further purification.

$^1$H NMR (400 MHz, D$_2$O): 1.26 (s, 9H), 2.12 (tt, J=21.2 Hz, 7.1 Hz, 1H), 3.09-3.24 (m, 4H), 3.94-4.00 (m, 1H), 4.22 (dd, J=−13.7 Hz, 9.6 Hz, 1H), 4.57-4.64 (m. 1H), 7.84 (dd, J=8.6 Hz, 6.1 Hz, 1H), 8.40 (d, J=8.1 Hz, 1H), 8.50 (d, J=−6.1 Hz, 1H), 8.69 (s, 1H). $^{31}$P{$^1$H} NMR (400 MHz, D$_2$O): δ 17.20-17.28 (m, 2P).

The entire sample of 14 was dissolved in water. An equal volume of TFA was slowly added, and the solution was stirred at room temperature for 3 hours. According to NMR, 100% yield is achieved of 16. The solvent was then removed in vacuo, and the resulting solids were washed with diethyl ether and methanol, filtered, and dried, yielding 16 as white crystals. 16 was then used without further purification.

$^1$H NMR (400 MHz, D$_2$O): δ 2.18-2.36 (brt, 1H), 2.92 (brt, 1H), 3.14-3.28 (m, 3H), 4.16-4.24 (m, 1H), 4.60 (dd, J=13.5 Hz, 9.5 Hz, 1H), 7.79 (dd, J=8.7 Hz, 6.1 Hz, 1H), 8.37 (d, J=8.2 Hz, 1H), 8.44 (d, J=6.1 Hz, 1H), 8.64 (s, 1H). $^{31}$P{$^1$H} NMR (400 MHz, D$_2$O): δ 17.2-18.0 (m, 2P).

Synthesis of 3-{3-[(tert-butoxycarbonyl)amino]-2-hydroxypropyl}-1-(2-hydroxy-2,2-diphosphonoethyl)-1H-imidazol-3-ium 9.8 mg of 29 was dissolved in 1 mL H$_2$O and pH adjusted to 7.4 with Na$_2$CO$_3$. To this solution was added 32.7 mg of 4 in minimal MeOH. The reaction mixture was heated at 60° C. overnight, yielding compound 31 by $^{31}$P NMR and ESI-MS.

$^{31}$P NMR (400 MHz, D$_2$O): δ 14.11 (s). MS (negative ion ESI-MS, calculated 446.1093 m/z, found 443.9 m/z).

Synthesis of N-{3-[(tert-butoxycarbonyl)amino]-2-hydroxypropyl}-N-(3-hydroxy-3,3-diphosphonopropyl)-N-methylpentan-1-aminium 9.3 mg of 28 was dissolved in 1 mL H$_2$O and pH adjusted to 9.8 with Na$_2$CO$_3$. To this solution was added 27.1 mg of 4 in minimal MeOH. The reaction mixture was stirred at 50-60° C. for 2 weeks, yielding compound 32 by $^{31}$P NMR spectrum.

$^{31}$P NMR (400 MHz, D$_2$O): δ 16.82 (s).

Synthesis of (8)

The following synthesis and purification steps were performed under minimal lighting. 177 mg of 6 (0.4 mmol, 5 equiv) was dissolved in 2 mL of 0.1 N NaHCO$_3$. The pH of the solution was adjusted to 8.3 with Na$_2$CO$_3$. 41 mg of 5(6)-FAM, SE (7) (0.08 mmol, 1 equiv) was dissolved in 200 μL anhydrous DMF and then combined with water solution, forming a dark red-orange solution with small amount of precipitate. The pH was again adjusted to 8.1 with Na$_2$CO$_3$, causing the precipitate to dissolve, and the reaction mixture was stirred at room temperature for 3 hours.

The reaction mixture was directly placed on TLC plates with 100% MeOH as eluant. Free label moves quickly with the solvent, resulting in a yellow upper band, while all phosphorus containing compounds remain on the baseline, a dark orange band. The bottom band was extracted from the silica with HPLC water and Chelex (sodium form). The solution was centrifuged and concentrated in vacuo to yield dark red-orange solids.

The solids were dissolved in HPLC water and filtered through Nanosep 30K Omega filters. The solution was then purified by reverse-phase HPLC: Dynamax C18 (21.4 mm×25 cm) column, flow rate 8.0 mL/min, gradient as follows: 10% MeOH in 0.1 N TEAAc (pH 7) to 40% of 75% MeOH in 0.1 N TEAAc (pH 7) in 12 min, increasing to 70% of Buffer B in 100 min. Major peaks eluting at 27 and 75 minutes were collected and combined. Upon removal of buffer, product was precipitating out of solution. Thus, a second HPLC purification was performed with the same conditions as before but with TEAC buffers (pH 7.5). This allowed for basic conditions when buffer was removed in vacuo. To help remove excess TEA, the HPLC purified product was dissolved in water. To this solution was added ~10 excess of NaI in water. The solvent was removed in vacuo, yielding dark red solids. The solids were washed with acetone and centrifuged. The solids were then re-dissolved in water to help remove acetone and the solvent removed in vacuo to yield 8 as red solids. The final amount of 8 was calculated from UV absorption spectra with ϵ=73000 M$^{-1}$cm$^{-1}$ at pH 7.2 and the compound was lyophilized.

8 (as disodium, monotriethylammonium iodide salt): $^1$H NMR (400 MHz, D$_2$O): 3.33-3.39 (m, 2H), 3.43-3.66 (m, 2H), 4.08-4.42 (m, 3H), 4.72-4.80 (brd, 1H), 6.36-6.48 (m, 4H), 6.93 (d, 2H), 7.09 (s, 1H), 7.43 (s, 0.4H), 7.68-7.87 (m, 2H), 8.06 (s, 0.6 H), 8.37-8.56 (m, 2H), 8.69-8.78 (2 s, 1H). $^{31}$P{$^1$H} NMR (400 MHz, D$_2$O): δ 16.26 (d, J=23 Hz, 1P), 16.50 (d, J=23 Hz, 2P).

Synthesis and Separation of (9 and 10)

11 mg of 6 (0.2 mmol, 1 equiv) was dissolved in 1 mL H$_2$O and 1.5 mL 0.1 N NaHCO$_3$. The pH was adjusted to 8.4 with additional Na$_2$CO$_3$ to bring pH to 8.4. To this solution was added 100 mg of 7 (0.2 mmol, 1 equiv) in ~700 μL anhydrous DMF in darkness. After the addition of the label, the pH was again adjusted to 8.4 to increase solubility of the label. The reaction mixture was stirred at room temperature in darkness for 3 hours.

The solvent was then removed in vacuo, yielding bright reddish-orange solids. The unpurified product was then re-dissolved in water and purified by size exclusion chromatography with a Sephadex G10 column and eluted with 50 mM TEAAc. The bright orange compound can easily be seen traveling through the column. The first ~20 mL of compound eluted were analyzed by TLC with 100% MeOH and showed no traces of 5(6)-FAM (Rf 1.0).

The solvent of this fraction was then removed in vacuo and re-dissolved in 10% MeOH of 0.1 N TEAAc buffer (pH 7). The compound was then purified by reverse-phase HPLC under the following conditions: Dynamax C18 (21.4 mm×25 cm) column, flow rate 8.0 mL/min of 10% MeOH in 0.1 N TEAAc (pH 7) to 40% of 75% MeOH in 0.1 N TEAAcO (pH 7) in 12 min, increasing to 70% of 75% MeOH in 0.1 N TEAAc in 100 min, UV detection at 260 nm. 9 and 10 eluted at very different retention times, 27 and 44 minutes, respectively; each isomer was collected separately. Each fraction collected was analyzed by TLC (eluted with 100% MeOH) to ensure no traces of 5(6)-FAM was present. Each isomer was then concentrated in vacuo to remove buffer. The final amount of 9 and 10 was calculated from UV absorption spectra with ϵ=73000 M$^{-1}$cm$^{-1}$ at pH 7.2. The compounds were then lyophilized to yield bright reddish-orange solids.

9 (retention time of 44 minutes, as triethylammonium acetate salt): $^1$H NMR (400 MHz, D$_2$O): δ 3.37 (brt, 2H), 3.57 (dd, J=14.1 Hz, 6.7 Hz, 1H), 3.61-3.69 (m, 1H), 4.22-4.31 (m, 1H), 4.36-4.45 (m, 1H), 4.79 (d, 1H), 6.61-6.71 (m, 4H), 7.11 (d, J=9.2 Hz, 1H), 7.33 (d, J=8.0 Hz, 1H), 7.56 (s, 0.14H), 7.83 (t, J=7.2 Hz, 1H), 7.91 (d, J=8.1 Hz, 1H), 8.15 (s, 1H), 8.44 (d, J=8.3 Hz, 1H), 8.56 (d, J=5.9 Hz, 1H), 8.74 (s, 1H). $^{31}$P{$^1$H} NMR (500 MHz, D$_2$O): δ 16.47 (brs).

HRMS (positive ion MALDI gave the free acid molecular cation, calculated 715.1089 m/z, found 715.1055 m/z (negative ion MALDI, low resolution mass spectra, gave a major peak at 713).

10 (retention time of 27 minutes, as triethylammonium acetate salt): $^1$H NMR (400 MHz, D$_2$O): δ 3.27-3.37 (m, 2H), 3.44 (dd, J=14 Hz, 6.9 Hz, 1H), 3.58 (dd, J=14 Hz, 4.9 Hz, 1H), 4.19 (brs, 1H), 4.35 (dd, J=14 Hz, J=9.3 Hz, 1H), 6.60-6.73 (m, 4H), 7.04 (d, J=9.4 Hz, 2H), 7.53 (s, 1H), 7.81 (dd, J=8.2 Hz, 6.4 Hz, 1H), 7.88 (d, J=8.1 Hz, 1H), 7.95 (dd, J=8.0 Hz, 1.6 Hz, 1H), 8.43 (d, J=8.1 Hz, 1H), 8.53 (d, J=6.5 Hz, 1H), 8.70 (s, 1H). $^{31}$P{$^1$H} NMR (500 MHz, D$_2$O): δ 16.51 (brs).

HRMS (positive ion MALDI gave the free acid molecular cation, calculated 715.1089 m/z, found 715.1082 m/z).

HRMS (positive ion MALDI gave the free acid molecular cation, calculated 715.1089 m/z, found 715.1082 m/z).

Direct Synthesis of 9 from 5-FAM, SE

To first confirm isomer assignments, 9 was directly synthesized from 5-FAM, SE according to the procedure directly above. The compound was first purified by reverse-phase HPLC according to conditions described above, but no separation from free label was seen. The fluorescent compounds were collected and additionally purified on a Sephadex G10 column according to conditions above. $^1$H and $^{31}$P NMR spectra were exactly the same as 9 synthesized from 5(6)-FAM and isolated by HPLC separation.

Synthesis of (17)

The following synthesis and purification steps were performed under minimal lighting. 158 mg of 15 (0.3 mmol, 3 equiv) was dissolved in 1 mL of water. The pH of the solution was adjusted to 8.3 with Na$_2$CO$_3$. 53 mg of 5(6)-FAM, SE (7) (0.1 mmol, 1 equiv) was dissolved in 200 μL anhydrous DMF and then combined with water solution, forming a dark red-orange solution with small amount of precipitate. The pH was again adjusted to 8.1 with Na$_2$CO$_3$, causing the precipitate to dissolve, and the reaction mixture was stirred at room temperature overnight.

The reaction mixture was directly placed on TLC plates with 100% MeOH as eluant. Free label moves quickly with the solvent, resulting in a yellow upper band, while all phosphorus containing compounds remain on the baseline, a dark orange band. The bottom band was extracted from the silica with HPLC water and Chelex (sodium form). The solution was centrifuged and concentrated in vacuo to yield dark red-orange solids. The solution was then purified by HPLC: Dynamax C18 (21.4 mm×25 cm) column, flow rate 8.0 mL/min, gradient as follows: isocratic elution of 20% MeOH in 0.1 N TEAC (pH 7) for 12 min, linearly increasing to 100% of 70% MeOH in 0.1 N TEAC (pH 7) in 22 min, UV detection at 260 nm. Peaks eluting at 25-40 minutes were collected together as 17. The final amount of 17 was determined from UV absorption spectra (ε=73000 M$^{-1}$cm$^{-1}$ at pH 7.2), and the compound was lyophilized to yield bright red-orange solids.

17 (as triethylammonium acetate salt): $^1$H NMR (400 MHz, D$_2$O): δ 3.27-3.62 (m, 3H), 4.03-4.40 (m, 2H), 6.42 (m, 4H), 6.92 (dd, J=9.5 Hz, 3.5 Hz, 2H), 7.10 (d, J=8.1 Hz, 1H), 7.42 (s, 0.4H), 7.70-7.86 (m, 2H), 8.06 (s, 0.6H), 8.27 (brs, 1H), 8.46-8.63 (m, 2H). $^{31}$P{$^1$H} NMR (400 MHz, D$_2$O): δ 15.28 (brs, 1P).

HRMS (positive ion MALDI gave the free acid molecular cation, calculated 679.1335 m/z, found 679.1321 m/z).

Direct Synthesis of 18 and 19 from 5- and 6-FAM, SE, Respectively

Single isomers of 17 were synthesized directly from isomerically pure starting materials (5-FAM, SE or 6-FAM, SE) according to method above used for isomeric mixtures.

18 (retention time 28 minutes, as triethylammonium acetate salt): $^1$H NMR (400 MHz, D$_2$O): δ 3.39-3.52 (m, 2H), 3.55-3.63 (m, 1H), 4.14-4.23 (m, 1H), 4.30-4.40 (m, 1H), 6.43-6.60 (m, 4H), 7.04 (d, J=9.0 Hz, 2H), 7.25 (d, J=8.2 Hz, 1H), 7.77-7.86 (m, 2H), 8.08 (s, 1H), 8.23-8.33 (brs, 1H), 8.45-8.62 (m, 2H).

HRMS positive ion MALDI gave the free acid molecular cation, calculated 679.1324 m/z, found 679.1356 m/z).

19 (retention time 25 minutes, as triethylammonium acetate salt): $^1$H NMR (400 MHz, D$_2$O): δ 3.31-3.45 (m, 2H), 3.47-3.55 (m, 1H), 4.05-4.15 (m, 1H), 4.24-4.34 (m, 1H), 6.45-6.59 (m, 4H), 7.00 (d, J=9.0 Hz, 2H), 7.48 (s, 1H), 7.71-7.80 (m, 2H), 7.85 (dd, J=8.1 Hz, J=1.7 Hz, 1H), 8.21-8.27 (m, 1H), 8.47-8.55 (m, 2H).

HRMS positive ion MALDI gave the free acid molecular cation, calculated 679.1324 m/z, found 679.1321 m/z).

Synthesis of (20)

53 mg of 16 (0.1 mmol, 3.3 equiv) was dissolved in 0.5 mL HPLC water and 0.5 mL of 0.1 N NaHCO$_3$. The pH was adjusted to 8.3 with Na$_2$CO$_3$. 18 mg of 5(6)-FAM, SE (7) (0.03 mmol, 1 equiv) was dissolved in 100 μL anhydrous DMF and then combined with water solution, forming a dark red-orange solution with small amount of precipitate. The pH was again adjusted to 8.9 with Na$_2$CO$_3$, causing the precipitate to dissolve, and the reaction mixture was stirred at room temperature overnight.

The reaction mixture was purified by TLC with 100% MeOH as the eluant. The dark orange bottom band was extracted from silica with water and Chelex (sodium form). The solution was centrifuged and solvent removed in vacuo, yielding dark red solids. The solids were dissolved in 20% MeOH in 0.1 N TEAAc buffer (pH 7) and filtered through Nanosep 30K Omega filters. The solution was then purified by HPLC: Dynamax C18 (21.4 mm×25 cm) column, flow rate 8.0 mL/min, gradient as follows: isocratic elution of 20% MeOH in 0.1 N TEAC (pH 7) for 12 min, linearly increasing to 100% of 70% MeOH in 0.1 N TEAC (pH 7) in 22 min, UV detection at 260 nm. Peaks eluting from 27-45 minutes were collected as 20. The final amount of 20 was determined from UV absorption spectra (ε=73000 M$^{-1}$cm$^{-1}$ at pH 7.2), and the compound was lyophilized to yield red-orange solids.

20 (as triethylammonium acetate salt): $^1$H NMR (400 MHz, D$_2$O): δ 2.07-2.27 (m, 1H), 3.10-3.27 (m, 2H), 3.35 (dd, J=14.2 Hz, 6.8 Hz, 0.4H), 3.44-3.53 (m, 1H), 3.60 (dd, J=14.2 Hz, 4.7 Hz, 0.6H), 4.08-4.16 (m, 0.4H), 4.18-4.25 (m, 0.6H), 4.25-4.40 (m, 1H), 4.71-4.77 (m, 1H), 6.40-6.52 (m, 4H), 6.96 (dd, J=8.1 Hz, 4.1 Hz, 2H), 7.17 (d, J=8.1 Hz, 0.6H), 7.44 (s, 0.4H), 7.72 (d, J=8.1 Hz, 0.4H), 7.76-7.86 (m, 2H), 8.07 (d, J=1.7 Hz, 0.6 H), 8.38 (t, J=8.7 Hz, 1H), 8.47 (d, J=5.9 Hz, 1H), 8.53 (d, J=6.1 Hz, 1H), 8.67-8.71 (2 s, 1H). $^{31}$P{$^1$J} NMR (400 MHz, D2O): δ 16.51 (brs).

HRMS (positive ion MALDI gave the free acid molecular cation, calculated 699.1139 m/z, found 699.1137 m/z).

Synthesis of (23)

11.2 mg of 6 was dissolved in 0.5 mL H$_2$O and pH adjusted to 9 with Na$_2$CO$_3$. To this solution was added 5 mg of RhR-X, SE 21 in 250 µL DMF, and the reaction mixture stirred overnight. The solvent was then concentrated under vacuum, and the resulting solids were dissolved in $H_2O$ and purified by TLC (eluted with 100% MeOH). The band at the origin was extracted with $H_2O$, and the solution was centrifuged and solvent removed in vacuo. The solids are dissolved in $H_2O$, and the solution is then purified by HPLC: Beckman Ultrasphere C18 (250×10 mm), flow rate 6.0 mL/min, gradient as follows: isocratic elution of 20% MeOH in 0.1 N TEAC (pH 7) for 5 min, linearly increasing to 100% of 75% MeOH in 0.1 N TEAC (pH 7) in 6 min, UV detection at 260 nm. Peak eluting at 12 minutes were collected as 23. The final amount of 23 was determined from UV absorption spectra ($\epsilon=114850$ $M^{-1}cm^{-1}$ at pH 7.5).

23 (as triethylammonium carbonate salt): $^1$H NMR (400 MHz, $D_2O$): δ 1.26 (m, 2H), 1.38 (m, 2H), 2.10 (t, 2H), 3.01-3.09 (brm, 4H), 3.38-3.49 (brm, 8H), 3.99 (m, 1H), 4.12 (m, 1H), 4.51 (1H), 6.73 (s, 2H), 6.79 (d, 2H), 6.86. (d, 2H), 7.50 (d, 1H), 7.71 (t –1H), 8.09 (d, 1H), 8.35-8.45 (brm, 2H), 8.66 (s, 1H).

MS (positive ion ESI-MS gave the free acid molecular cation, calculated 1011.2913 m/z, found 1008.28 m/z).

Synthesis of (24)

10.9 mg of 15 was dissolved in 0.5 mL of 0.1 N $NaHCO_3$ buffer, and pH adjusted to 8.7 with $Na_2CO_3$. To this solution was added 5 mg of Rhodamine Red-X, SE 21 in 500 µL DMF, and the reaction mixture stirred overnight. The solution was then placed on a TLC plate (7 cm×20 cm), and eluted 3× with MeOH. The bottom band was extracted with H2O, and the solution was centrifuged and solvent removed in vacuo. The solids were dissolved in 20% MeOH in 0.1 N TEAAc buffer (pH 7) and filtered through Nanosep 30K Omega filters. The solution is then purified by HPLC: Beckman Ultrasphere C18 column (250×10 mm), flow rate 4.0 mL/min, UV at 260 nm, gradient as follows: 20% MeOH in 0.1 N TEAC (pH 7.5) for 4 min, linearly increasing to 100% of 70% MeOH in 0.1 N TEAC (pH 7.5) in 19 min, UV detection at 260 nm. The final amount of 24 was determined from UV absorption spectra ($\epsilon=114850$ $M^{-1}cm^{-1}$ at pH 7.5).

24 (as triethylammonium carbonate salt): $^1$H NMR (400 MHz, $D_2O$): δ 1.27 (m, 2H), 1.39 (m, 2H), 2.09 (t, 2H), 2.89-2.99 (brm, 4H), 3.10-3.16 (brm, 2H), 3.20-3.27 (brm, 1H), 3.38-3.49 (brm, 8H), 3.95 (m, 1H), 4.14 (m, 1H), 4.51 (1H), 6.63 (s, 2H), 6.72 (d, 2H), 6.79. (d, 2H), 7.43 (d, 1H), 7.73 (t, 1H), 8.08 (d, 1H), 8.25-8.30 (brm, 1H), 8.42 (d, 2H), 8.50 (d, 1H). $^{31}$P NMR (500 MHz, $D_2O$): 15.11 (s).

HRMS (positive ion MALDI gave the free acid molecular cation, calculated 975.3148 m/z, found 974.3118 m/z).

Synthesis of (25)

36.2 mg of 16 was dissolved in 3 mL 0.1 N $NaHCO_3$ with pH adjusted to 8.3 with $Na_2CO_3$. 10 mg of AMCA-X, SE in 400 µL anhydrous DMF was added, and the pH re-adjusted to 8.3 with $Na_2CO_3$. The reaction mixture was stirred in darkness at rt overnight. The reaction mixture was purified by TLC with 100% MeOH as the eluant. The bottom band was extracted from silica with water and Chelex (sodium form). The solution was centrifuged and solvent removed in vacuo. The solids are dissolved in 20% MeOH in 0.1 N TEAAc buffer (pH 7) and filtered through Nanosep 30K Omega filters. The solution is then purified by HPLC: Dynamax C18 (21.4 mm×25 cm) column, flow rate 6.0 mL/min, gradient as follows: isocratic elution of 20% MeOH in 0.1 N TEAC (pH 7) for 12 min, linearly increasing to 100% of 70% MeOH in 0.1 N TEAC (pH 7) in 22 min, UV detection at 260 nm. Peaks eluting from 27-45 minutes were collected as 25. The final amount of 25 was determined from UV absorption spectra ($\epsilon=16000$ $M^{-1}cm^{-1}$ at pH 7.5).

25 (as triethylammonium carbonate salt): $^1$H NMR (400 MHz, $D_2O$): δ 1.36 (m, 2H), 1.45 (m, 2H), 2.04-2.19 (m, 3H), 2.21 (d, 2H), 3.2-3.4 (brm, 5 H), 3.68-3.77 (m, 1H), 3.99-4.06 (brm, 1H), 4.21 (dd, 1H), 4.59 (dd, 1H), 6.48-6.51 (brm, 1 H), 6.62-6.67 (brm, 1 H), 7.41-7.46 (brm, 1H), 7.78 (dd, 1H), 8.37 (d, 1H), 8.43, (d, 1H), 8.65 (s, 1H). $^{31}$P NMR (500 MHz, $D_2O$): 17.47 (s).

Synthesis of (27)

5 mg of 6 in 200 µL of $H_2O$ (pH adjusted to 8.3 with $Na_2CO_3$) was added to 1 mg of Alexa Fluor® 647, succinimidyl ester (AF647, SE 26) in 50 µL anhydrous DMF, and the solution was stirred overnight. The solvent was concentrated under vacuum, and the resulting blue residue was dissolved in 20% MeOH in 0.1 N TEAAc buffer (pH 5). The solution was purified by semi-preparative HPLC under the following conditions: Beckman Ultrasphere C18 (250×10 mm) column, flow rate 4.0 mL/min of 0.1 N TEAAc buffer (pH 5) for 5 min, linearly increasing to 40% of 70% MeOH in 0.1 N TEAAc buffer (pH 5) in 25 min, V detection at 260 and 598 nm. Peaks eluting at 17 min were collected as 27. The final amount of 27 is determined by UV absorption spectra ($\epsilon=240000$ $M^{-1}cm^{-1}$ at pH 7), and the solution was lyophilized to yield blue-purple solids.

MS (positive ion ESI-MS gave the free acid molecular cation, calculated 1198.2410 m/z, found 1197.1 m/z).

Discussion

The inventors describe a new linking strategy centered on the coupling of a bisphosphonate or phosphonocarboxylate compound via a tertiary or heterocyclic nitrogen, such as the nitrogen of the pyridine ring in (1-hydroxy-2-pyridin-3-ylethane-1,1-diyl)bis(phosphonic acid) 1, to N-t-BOC-protected 1,2-epoxy-3-aminopropane 4 (easily prepared in 85% yield by conventional protection of commercially available allylamine with tert-butoxycarbonyl anhydride, followed by epoxidation using MCPBA (31). The reaction proceeds under startlingly mild conditions: the bisphosphonate or phosphonocarboxylate compound and the oxirane reagent are stirred overnight in aqueous methanol at 35° C., resulting in clean, quantitative conversion to the drug-linker conjugate, which after conventional deprotection of t-BOC with TFA, yields 1-(3-amino-2-hydroxy-propyl)-3-(2-hydroxy-2,2-diphosphonoethyl)pyridinium trifluoroacetate (6). With slight modifications to these reaction conditions, N-alkylation of compounds such as [hydroxy(1H-imidazol-1-yl)methylene]bis(phosphonic acid) and {1-hydroxy-3-[methyl (pentyl)amino]propane-1,1-diyl}bis(phosphonic acid) have also been accomplished.

This remarkably facile reaction in water, generating the desired N+ species, permits clean, quantitative 'in situ' attachment of drug-linker to various moieties, such as fluorescent or near-IR labels or other agents for various applications such as drug delivery systems, without the need for any external reagent or catalyst. As such it should be broadly applicable to functionalization of water-soluble pyridyl-containing compounds, with (e.g. 1) or without therapeutic activity (e.g. (1-hydroxy-2-pyridin-4-ylethane-1,1-diyl)bis(phosphonic acid)), and other tertiary or heterocyclic nitrogen-containing compounds. Also advantageous is the formation of a secondary OH in the drug linking step, providing a hydrophilic group in mid-linker, which may aid in increasing the aqueous solubility of the conjugate. This also gives rise to a chiral center at the C-2 of the linker, which may prove to be an integral structural aspect for determining pharmacological properties of drug-like products.

Also key to this reaction is its regioselectivity. Chuiko et al previously reported O-alkylation of a bisphosphonic acid with diethyl-oxiranylmethylamine in aqueous conditions near neutral pH with heating (60-70° C.) (6). However, the inventors discovered that at this temperature, <10% O-alkylation and >90% N-alkylation of compound 1 was observed. By lowering the temperature of the reaction mixture to 40° C., the inventors were able to afford N-alkylated analog of 1 cleanly. Generating O-alkylated analogs of bisphosphonates or phosphonocarboxylates may lower the parent compound's affinity to bone, thus adversely affecting key properties of the parent compound that may be necessary to retain for their application as imaging probes.

After deprotection in TFA of analog 5, the unmasked amine 6 is reacted with a mixture of 5- and 6-FAM isomers in activated succinimidyl form (5(6)-FAM, SE 7). The individual 5-(9) and 6-(10) isomers of the resulting fluorescently labeled drug analog, readily distinguished by $^1$H NMR, are easily isolated by TLC followed by preparative reverse-phase HPLC (9 is more mobile under the conditions chosen), or HPLC and size-exclusion chromatography. To confirm the isomer assignment, the synthesis and purification is repeated replacing the 5(6)-FAM, SE by pure 5-FAM, SE, which permitted unequivocal assignment of the $^1$H NMR peaks (particularly in the aromatic region) and HPLC elution order. The $^{31}$P NMR spectra for the separated isomers are identical with a broad peak at ~16-17 ppm. The red-orange products are readily soluble in aqueous media near neutral or slightly basic pH. The UV-visible spectra are very similar in form to those of the parent 5(6)-FAM, dominated by the major peak at 492 nm, apart from a small increase in molar absorptivity near 260 nm, attributed to the presence of the pyridinium chromophore of 1. The emission spectra of the FAM-labeled products in phosphate buffer, pH 7.2, show a maximum emission at ~520 nm where FAM-isomers exhibit about 75-80% relative quantum yields compared to 5(6)-FAM. This slight decrease in fluorescence could be attributed to minimal exposure to light during work-up of the compounds or may be an inherent characteristic of the inventors' compounds.

TABLE 1

Characterization of the fluorescent Labeled isomers 9 and 10

| Compound | 9 | 10 |
|---|---|---|
| $^1$H NMR | δ 3.37 (brt, 2H), 3.57 (dd, J = 14.1 Hz, 6.7 Hz, 1H), 3.61-3.69 (m, 1H), 4.22-4.31 (m, 1H), 4.36-4.45 (m, 1H), 4.79 (d, 1H), 6.61-6.71 (m, 4H), 7.11 (d, J = 9.2 Hz, 2H), 7.33 (d, J = 8.0 Hz, 1H), 7.56 (s, 0.14 H), 7.83 (t, J = 7.2 Hz, 1H), 7.91 (d, J = 8.1 Hz, 1H), 8.15 (s, 1H), 8.44 (d, J = 8.3 Hz, 1H), 8.56 (d, J = 5.9 Hz, 1H), 8.74 (s, | δ 3.27-3.37 (m, 2H), 3.44 (dd, J = 14 Hz, 6.9 Hz, 1H), 3.58 (dd, J = 14 Hz, 4.9 Hz, 1H), 4.19 (brs, 1H), 4.35 (dd, J = 14 Hz, J = 9.3 Hz, 1H, 6.60-6.73 (m, 4H), 7.04 (d, J = 9.4 Hz, 2H), 7.53 (s, 1H), 7.81 (dd, J = 8.2 Hz, 6.4 Hz, 1H), 7.88 (d, J = 8.1 Hz, 1H), 7.95 (dd, J = 8.0 Hz, 1.6 Hz, 1H), 8.43 (d, J = 8.1 Hz, 1H), |
| | 1H). | 8.53 (d, J = 6.5 Hz, 1H), 8.70 (s, 1H). |
| $^{31}$P NMR | δ 16.47 (brs). | δ 16.51 (brs). |
| HRMS: positive ion MALDI (m/z) | Calculated 715.1089, found 715.1055. | Calculated 715.1089, found 715.1082. |
| UV $\lambda_{max}$ (nm) | 492 | 492 |
| Emission $\lambda_{max}$ (nm) | 523 | 520 |
| HPLC retention time (minutes) | 44 | 27 |

A highly selective fluorescent probe derived from R-glycidol and 5-FAM, SE and 5(6)-FAM, SE, which also contained a benzenesulfonamide ligand to bind with high affinity to human carbonic anhydrase II (HCA II), was previously reported (4). Chen et al. attached the epoxide moiety (from glycidol) to the fluorescent label via an ester bond, a linkage known to be hydrolytically unstable under physiological conditions, and subsequently conjugated the epoxide probe (in slight excess) to the heterocylic nitrogen of a histidine residue of HCA II (4).

In comparison, the current approach reverses the order of Chen (4) by first opening the epoxide by the heterocyclic (or tertiary) nitrogen, followed by conjugation to the imaging agent. This method generates a more hydrolytically stable amide bond between the label and the parent compound. The labeled drug analogs 9 and 10 are stable in neutral conditions at room temperature for at least 24 hours by $^1$H NMR and analytical TLC (eluted with 100% MeOH, decomposition product will have Rf of 1.0). However, a similar drug analog that contained an ester bond between the drug and label showed decomposition by analytical TLC within a few hours under the same conditions.

Although the epoxide may first be attached to the imaging agent (preferably via an amide bond) and then conjugated to the heterocyclic or tertiary nitrogen, one must consider the cost of the imaging agent starting material, which often varies but may be as high as ~$900 for 5 milligrams. Thus, synthesizing an imaging agent conjugated directly to the epoxide (to be subsequently attached to the parent drug or compound) may be less cost efficient, especially in cases where a slight excess of the epoxide may be needed for N-alkylation reactions (4), than synthesizing the N-alkylated analog of the parent compound first, which can then be conjugated to the commercially available imaging agents in a 1:1 ratio.

At present, the individual 5- and 6-FAM, SE isomers are much more expensive than the commercially available isomer mixture, although separation schemes based on derivatization have been recently proposed (26). In addition, separation of the isomers have reportedly been achieved by reverse phase HPLC or by utilizing Biotage FLASH 75 system (which reportedly allows for gram scale separations) but slight hydrolysis of the succinimidyl esters was seen (1). However, the inventors found that separation of the isomeric product mixture was much more cost effective than either separation of starting material ester or synthesis from pure isomers themselves.

Additionally, this type of technology provides for the synthesis of phosphonates labeled with other fluorescent labels, such as AMCA-X and Rhodamine Red-X, and near-infrared labels, such as Alexa Fluor® 647. The compounds are synthesized and purified similar to the method described for FAM-labeled products. The phosphonates are characterized by mass spectrometry and NMR, UV absorption, and fluorescence emission spectra.

TABLE 2

UV absorption and fluorescence emission spectra of labeled compounds.

| Compound | Absorption $\lambda_{max}$ (nm) | Emission $\lambda_{max}$ (nm) |
| --- | --- | --- |
| 5(6)-PAM | 492 | 516 |
| 8 | 493 | 518 |
| 9 | 493 | 523 |
| 10 | 493 | 520 |
| 17 | 493 | 520 |
| 18 | 493 | 522 |
| 19 | 493 | 516 |
| 20 | 493 | 518 |
| 23* | 567 | 589 |
| 24* | 567 | 587 |
| 25** | 346 | — |
| 27*** | 648 | 666 |

All UV spectra taken on DU 800 spectrophotometer and emission spectra taken on Jobin Yvon Horiba FluoroMax-3 fluorometer. Samples in 0.1 or 0.05N phosphate buffer, pH 7.0; excitation wavelength at 490 nm unless otherwise noted.
*Samples in 0.1N phosphate buffer, pH 7.5; excitation wavelength at 520 nm.
**Sample in 0.01N phosphate buffer, pH 7.5.
***Sample in 0.1N phosphate buffer pH 7.0; excitation wavelength at 600 nm.

Obviously, many modifications and variation of the invention as hereinbefore set forth can be made without departing from the spirit and scope thereof and therefore only such limitations should be imposed as are indicated by the appended claims.

All patent and literature references cited in the present specification are hereby incorporated by reference in their entirety.

REFERENCES

The following references are cited herein. The entire disclosure of each reference is relied upon and incorporated by reference herein.

1. Adamczyk, M.; Fishpaugh, J. R.; Heuser, K. J., Preparation of Succinimidyl and Pentafluorophenyl Active Esters of 5- and 6-Carboxyfluorescein. *Bioconjugate Chemistry* 1997, 8, (2), 253-255.
2. Bagi, C. M., Targeting of therapeutic agents to bone to treat metastatic cancer. *Advanced Drug Delivery Reviews* 2005, 57, (7), 995-1010.
3. Bertrand, R.; Derancourt, J.; Kassab, R., Fluorescence Characterization of Structural Transitions at the Strong Actin Binding Motif in Skeletal Myosin Affinity Labeled at Cysteine 540 with Novel Spectroscopic Cysteaminyl Mixed Disulfides. *Biochemistry* 2000, 39, (47), 14626-14637.
4. Chen, G.; Heim, A.; Riether, D.; Yee, D.; Milgrom, Y.; Gawinowicz Mary, A.; Sames, D., Reactivity of functional groups on the protein surface: development of epoxide probes for protein labeling. *Journal of the American Chemical Society* 2003, 125, (27), 8130-3.
5. Cheng, F.; Oldfield, E., Inhibition of Isoprene Biosynthesis Pathway Enzymes by Phosphonates, Bisphosphonates, and Diphosphates. *Journal of Medicinal Chemistry* 2004, 47, (21), 5149-5158.
6. Chuiko, A. L.; Filonenko, L. P.; Borisevich, A. N.; Lozinskii, M. O., Synthesis and properties of hydroxyaminoalkyl esters of (hydroxyethylidene)bis[phosphonic acid]. *Zhurnal Obshchei Khimii* 1993, 63, (5), 1070-4.
7. Clezardin, P.; Ebetino, F. H.; Fournier, P. G. J., Bisphosphonates and Cancer-Induced Bone Disease: Beyond Their Antiresorptive Activity. *Cancer Research* 2005, 65, (12), 4971-4974.
8. Ebetino, F. H.; Roze, C. N.; McKenna, C. E.; Barnett, B. L.; Dunford, J. E.; Russell, R. G. G.; Mieling, G. E.; Rogers, M. J., Molecular interactions of nitrogen containing bisphosphonates within farnesyl diphosphate synthase. *Journal of Organometallic Chemistry* 2005, 690, (10), 2679-2687.
9. Giepmans, B. N. G.; Adams, S. R.; Ellisman, M. H.; Tsien, R. Y., The Fluorescent Toolbox for Assessing Protein Location and Function. *Science* (Washington, D.C., United States) 2006, 312, (5771), 217-224.
10. Gumbleton, M.; Stephens, D. J., Coming out of the dark: the evolving role of fluorescence imaging in drug delivery research. *Advanced Drug Delivery Reviews* 2004, 57, (1), 5-15.
11. Kavanagh, K. L.; Guo, K.; Dunford, J. E.; Wu, X.; Knapp, S.; Ebetino, F. H.; Rogers, M. J.; Russell, R. G. G.; Oppermann, U., The molecular mechanism of nitrogen-containing bisphosphonates as antiosteoporosis drugs. *Proceedings of the National Academy of Sciences of the United States of America* 2006, 103, (20), 7829-7834.
12. Kotsikorou, E.; Oldfield, E., A Quantitative Structure-Activity Relationship and Pharmacophore Modeling Investigation of Aryl-X and Heterocyclic Bisphosphonates as Bone Resorption Agents. *Journal of Medicinal Chemistry* 2003, 46, (14), 2932-2944.
13. Kutyavin, I. V.; Lokhov, S. G.; Afonina, I. A.; Dempcy, R.; Gall, A. A.; Gorn, V. V.; Lukhtanov, E.; Metcalf, M.; Mills, A.; Reed, M. W.; Sanders, S.; Shishkina, I.; Vermeulen, N. M. J., Reduced aggregation and improved specificity of G-rich oligodeoxyribonucleotides containing pyrazolo [3,4 d]pyrimidine guanine bases. *Nucleic Acids Research* 2002, 30, (22), 4952-4959.
14. Li, L.; Kracht, J.; Peng, S.; Bernhardt, G.; Elz, S.; Buschauer, A., Synthesis and pharmacological activity of fluorescent histamine H2 receptor antagonists related to potentidine. *Bioorganic & Medicinal Chemistry Letters* 2003, 13, (10), 1717-1720.
15. Martin, M. B.; Arnold, W.; Heath, H. T., III; Urbina, J. A.; Oldfield, E., Nitrogen containing bisphosphonates as carbocation transition state analogs for isoprenoid biosynthesis. *Biochemical and Biophysical Research Communications* 1999, 263, (3), 754-758.
16. Mende, I.; Hoffmann, P.; Wolf, A.; Lutterbuese, R.; Kopp, E.; Baeuerle, P. A.; de Baey, A.; Kufer, P., Highly efficient antigen targeting to M-DC8+ dendritic cells via FcgRIII/CD 16-specific antibody conjugates. *International Immunology* 2005, 17, (5), 539-547.
17. Mignogna, M. D.; Lo Russo, L.; Fedele, S.; Ciccarelli, R.; Lo Muzio, L. Case 2. *Osteonecrosis of the jaws associated with bisphosphonate therapy*; Section of Oral Medicine, Dept of Odontostomatological and Maxillofacial Sciences, University Federico II, Naples, Italy: United States, 2006; pp 1475-7.
18. Nancollas, G. H.; Tang, R.; Phipps, R. J.; Henneman, Z.; Gulde, S.; Wu, W.; Mangood, A.; Russell, R. G. G.; Ebetino, F. H., Novel insights into actions of bisphosphonates on bone: Differences in interactions with hydroxyapatite. *Bone* (San Diego, Calif., United States) 2006, 38, (5), 617-627.
19. Neville-Webbe, H. L.; Holen, I.; Coleman, R. E., The anti-tumour activity of bisphosphonates. *Cancer Treatment Reviews* 2002, 28, (6), 305-319.
20. Rodan, G. A.; Martin, T. J., Therapeutic approaches to bone diseases. *Science* (Washington, D.C.) 2000, 289, (5484), 1508-1514.
21. Russell, R. G. G.; Rogers, M. J., Bisphosphonates: from the laboratory to the clinic and back again. *Bone* (New York) 1999, 25, (1), 97-106.

22. Schirmer, I.; Peters, H.; Reichart, P. A.; Durkop, H., Bisphosphonates and osteonecrosis of the jaw. *Mund-, Kiefer-und Gesichtschirurgie: MKG* 2005, 9, (4), 239-45.
23. Stephens, D. J.; Allan, V. J., Light microscopy techniques for live cell imaging. *Science* (Washington, D.C., United States) 2003, 300, (5616), 82-86.
24. Taha, E. A.; Youssef, N. F., Spectrophotometric determination of some drugs for osteoporosis. *Chemical & Pharmaceutical Bulletin* 2003, 51, (12), 1444-1447.
25. Thompson, K.; Rogers, M. J.; Coxon, F. P.; Crockett, J. C., Cytosolic entry of bisphosphonate drugs requires acidification of vesicles after fluid-phase endocytosis. *Molecular Pharmacology* 2006, 69, (5), 1624-1632.
26. Ueno, Y.; Jiao, G.-S.; Burgess, K., Preparation of 5- and 6-carboxyfluorescein. *Synthesis* 2004, (15), 2591-2593.
27. Ung, A. T.; Pyne, S. G., Synthesis of fluorescent and biotinylated analogs of (1R,2S,3R)-2-acetyl-4(5)-(1,2,3,4-tetrahydroxybutyl)imidazole. *Tetrahedron Letters* 1996, 37, (34), 6209-6212.
28. van Beek, E. R.; Lowik, C. W.; Ebetino, F. H.; Papapoulos, S. E., Binding and antiresorptive properties of heterocycle-containing bisphosphonate analogs: structure activity relationships. *Bone* 1998, 23, (5), 437-42.
29. Waggoner, A., Fluorescent labels for proteomics and genomics. *Current Opinion in Chemical Biology* 2006, 10, (1), 62-66.
30. Rocheblave, L.; Bihel, F.; De Michelis, C.; Priem, G.; Courcambeck, J.; Bonnet, B.; Chermann, J.-C.; Kraus, J.-L. *Journal of Medicinal Chemistry* 2002, 45, (15), 3321-3324.
31. White, S. S.; Haitao, L.; Marsh, R. J.; Piper, J. D.; Leonczek, N. d.; Nicolaou, n.; Bain, A. J.; Ying, L.; Klenerman, D., *Journal of American Chemical Society* 2006, 128, (35) 11423-11432.

What is claimed is:

1. A compound of the formula $R^2CH_2CH(OH)(CH_2)_nR^1$, wherein:
said compound comprises a C3 or longer alkyl chain, $1 < n < 12$,
said $R^2$ is

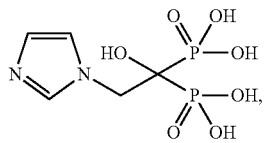

wherein $R^2$ is conjugated to a compound $CH_2[O]CH(CH_2)_n R^1$ via the nucleophilic nitrogen of $R^2$,
said $R^1$ group is a group selected from an amino group, $NH_2$, NHtBOC, a protected amino group, a hydroxyl, a halogen atom, and an oxirane, wherein said $R^1$ group is selected from the group consisting of a reactive group and a protected form of the reactive group that can be linked to a second compound.

2. The compound of claim 1 wherein the tertiary carbon in the $-CH_2CH(OH)(CH_2)_n-$moiety is racemic.
3. The compound of claim 1 wherein the tertiary carbon in the $-CH_2CH(OH)(CH_2)_n-$moiety is substantially pure as an R or S isomer.
4. The compound of claim 1 wherein n is 1 and $R^1$ is $NH_2$.
5. The compound of claim 1 wherein n is 1 and $R^1$ is a protected amino group.
6. The compound of claim 1 wherein n is 1 and $R^1$ is NHtBOC.

7. The compound of claim 1 wherein n is 2 and $R^1$ is an oxirane group.
8. A method of synthesizing the compound of claim 1 comprising reacting a primary oxirane $CH_2[O]CH-(CH_2)_n-R^1$ with a compound containing a group capable of reacting with an oxirane.
9. The method of claim 8 wherein n is 1 and $R^1$ is NHtBOC, and the tBOC protecting group is removed after formation of the conjugate by reaction with trifluoroacetic acid in water, aqueous DMF, or aqueous MeOH.
10. A method of preparing the compound of claim 1 comprising:
(a) reacting an alkene comprising $CH_2=CH-(CH_2)_n-R^1$ wherein $1 < n < 12$, and $R^1$ is selected from a group consisting of an amino, $NH_2$, NHtBOC, a protected amino group, a hydroxyl, a halogen atom, and an oxirane wherein said $R^1$ is selected from the group consisting of a reactive group and a protected form of reactive group that can be linked to a second compound, and;
(b) oxidizing the alkene group to an oxirane using meta-chloroperbenzoic acid to form a compound formula

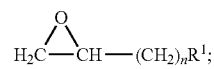

and
(c) conjugating the resulting compound of formula

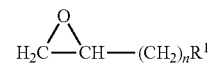

so as to form $R^2CH_2CH(OH)(CH_2)_n-R^1$, wherein $R^2$ is

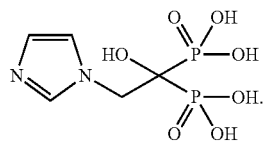 [SMILES: O=P(O)(O)C(O)(Cn1ccnc1)P(=O)(O)O]

11. The method of claim 10 wherein n is 1 and $R^1$ is NHtBOC.
12. A method of preparing a linker conjugated compound comprising:
(a) dissolving a first compound of formula:

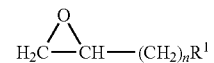

in a solvent, wherein said first compound comprises a C3 or longer alkyl chain in which $1 < n < 12$, and $R^1$ is selected from a group consisting of an amino, $NH_2$, NHtBOC, a protected amino group, a hydroxyl, a halogen atom, and an oxirane wherein said $R^1$ is selected from the group consisting of a reactive group and a protected form of the reactive group that can be linked to a second compound; and
(b) reacting a third compound with said first compound via a nucleophilic nitrogen of the third compound reacting with an oxirane group of the first compund, the third compound being

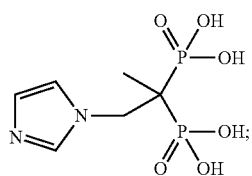 [SMILES: CC(Cn1ccnc1)(P(=O)(O)O)P(=O)(O)O]

and wherein said first compound is dissolved in a solvent.

13. The method of claim 12 wherein n is 1, $R^1$ is NHtBOC and wherein said said first compound is dissolved in a solvent comprising MeOH or DMF.

14. A method of preparing a modified compound comprising:
(a) dissolving a first compound of formula:

in a solvent wherein said first compound comprises a C3 or longer alkyl chain, in which $1<n<12$; and
(b) reacting a compound $R^2$ of Formula

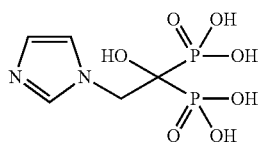 [SMILES: O=P(O)(O)C(O)(Cn1ccnc1)P(=O)(O)O]

with said first compound to form $R^2CH_2CH(OH)(CH_2)_n R^1$, wherein the compound $R^2$ is dissolved in an aqueous solvent; and
(c) reacting said $R^1$ group with a second drug moiety, a suitably functionalized bead, an immobilizing matrix, or a label, wherein said $R^1$ group is selected from the group consisting of an amino, a $NH_2$, a NHtBOC, a protected amino group, a hydroxyl, a halogen atom, and an oxirane wherein said $R^1$ group is selected from the group consisting of a reactive group and a protected form of the reactive group that can be linked to a drug moiety, functionalized bead, immobilizing matrix, or label.

15. The method of claim 14 wherein $R^1$ is $NH_2$ and said label comprises an imagining fluorophore containing an activated group or group capable of activation in situ.

16. The method of claim 14 wherein $R^1$ is $NH_2$ and the label comprises an imaging UV, visible, or near-IR fluorophore containing a succinimidyl ester.

17. The method of claim 14 wherein $R^1$ is $NH_2$ and said label comprises a FAM, Rhodamine Red-X, AMCA-X, Alexa Fluor® 647, or isomeric mixtures thereof, containing a succinimidyl ester.

18. The method of claim 14 wherein $R^1$ is $NH_2$ and the label comprises a mixture of 5-FAM, and 6-FAM isomers as succinimidyl esters, which are conjugated together to form a carboxamide group.

19. A compound synthesized according to any of claim 1, 8, 10, 12, or 14.

* * * * *